United States Patent [19]

Wood et al.

[11] Patent Number: 5,833,972
[45] Date of Patent: Nov. 10, 1998

[54] METHOD FOR ODOR REDUCTION

[75] Inventors: Louis L. Wood, Rockville; Gary J. Calton, Elkridge, both of Md.

[73] Assignee: Calwood Chemical Industries, Inc., Elkridge, Md.

[21] Appl. No.: 911,948

[22] Filed: Aug. 15, 1997

Related U.S. Application Data

[63] Continuation of Ser. No. 635,502, Apr. 22, 1996.

[51] Int. Cl.$^6$ ...................................................... A01N 25/12
[52] U.S. Cl. ........................ 424/76.5; 424/76.1; 424/76.2; 424/76.21; 424/76.6; 424/405; 424/406
[58] Field of Search ...................................... 424/405, 406, 424/65, 76.1, 76.2, 76.21, 76.5, 76.6

[56] References Cited

U.S. PATENT DOCUMENTS 5,408,028   4/1995   Wood et al. .............................. 528/328

*Primary Examiner*—Thurman K. Page
*Assistant Examiner*—Kathryne E. Shelborne
*Attorney, Agent, or Firm*—William S. Ramsey

[57] ABSTRACT

Imides reduce odors. Imides are especially efficient at reducing the odors of odoriferous an amine or ammonia. The imides may be incorporated in pads which are the recipients of odoriferous waste materials, dispersed in holding tanks or lagoons or dispersed over human and animal wastes. Polysuccinimide, copolymers of polysuccinimide, polyglutarimide and mixtures thereof are especially useful for the reduction of odors, especially of ammonia and an amine.

11 Claims, No Drawings

METHOD FOR ODOR REDUCTION

This application is a continuation of application Ser. No. 08/635,502, filed Apr. 22, 1996, pending.

FIELD OF THE INVENTION

This invention relates to the use of imides for the reduction of odors.

DESCRIPTION OF RELATED ART

Imides are normally formed by heating anhydrides with ammonia. Thus succinic anhydride and ammonia combine to form succinimide, while phthalic anhydride and ammonia form phthalimide. It is also well known in the art that imides are hydrolyzed by bases including ammonia or amine compounds. See for instance U.S. Pat. No. 5,408,028 and U.S. Pat. No. 5,175,285, where it is noted that imides can be reacted with amines in a mild manner and at low temperatures, thus avoiding degradation of polymer chains in which the imides may be present.

There are a number of well known syntheses of imides, the most elementary of which are found in standard organic textbooks while the subject continues to be of interest in the patent literature as exhibited by U.S. Pat. Nos. 4,839,461, 5,057,597, 5,221,733, 5,288,783, 5,315,010, 5,319,145, 5,371,179 and others.

Phthalimide and maleimide have long been useful in the synthesis of amines. Polysuccinimides and polyglutarimides have been found to be useful as precursors of polycarboxylates which are useful as fertilizers, detergent anti-redeposition agents, detergent builders, detergent co-builders, plant growth promotion agents, tartar control agents, corrosion inhibition agents, as dispersants of clay, coal, minerals, pigments, and as scale inhibition agents for calcium, barium and strontium salts, in dishwashing detergents, in boiler and cooling water, in superabsorbents, in cosmetic chemicals, and for reverse osmosis membranes. One of the primary characteristics that makes them valuable in this respect is the fact that they are biodegradable.

Polysuccinimides are heat resistant and only slightly soluble in water. They are readily hydrolyzed by bases to the corresponding polyaspartate. A partial hydrolysis of polyimides, such as polysuccinimide, polyglutarimide, and copolymers thereof or copolymers of mixtures thereof, can be achieved to allow the polysuccinimides to be soluble in water. The hydrolysis can be controlled, by controlling the amount of base added, to provide a polyimide that is soluble in water but retains imide for removal of odor. There are at least three general types of polysuccinimides based on the literature. They differ in molecular weight, branching and biodegradability. Polysuccinimides made from L-aspartic acid with an acid catalyst have the highest molecular weight, lowest branching and greatest biodegradability according to U.S. Pat. No. 5,457,176. Materials made from L-aspartic acid without a catalyst have an intermediate molecular weight, considerable branching and an acceptable level of biodegradability according to the Organization for Economic Cooperation and Development (OECD) standard. Materials made from maleic acid or an equivalent material, including fumaric acid, malic acid, monoamides or diamides of these compounds and ammonia have a low molecular weight, a high degree of branching and are not "readily biodegradable" according to the OECD standard.

A number of copolymers of polysuccinimide are also known. These copolymers contain monoamines, polyamines, carboxylic acids, polycarboxylic acids, and alcohols, both substituted and unsubstituted, as disclosed for instance in U.S. Pat. Nos. 5,466,760, 5,292,858, 5,442,038, 5,408,029, 5,142,062, 5,371,179, 5,028,689 and Foreign Pat. Appl. DE 4221875.

Odor control has been a significant problem for which there are very few solutions. Amines and ammonia are especially troublesome as odors. Their volatility makes them quite noticeable when even small amounts are released. U.S. Pat. No. 5,013,335 discloses the use of zeolites for control of ammonia odor. U.S. Pat. No. 5,211,870 discloses the use of zeolites in bar soaps to reduce odor. U. S. Pat. No. 4,988,505 discloses the use of antimony pentoxide to reduce the odor of amine containing gases. U.S. Pat. No. 5,135,664 discloses the use of pH to control the emissions of volatile amines in sludge. U.S. Pat. No. 5,135,743 discloses the use of boric acid and pine oil to reduce the odor of animal litter. U.S. Pat. No. 5,306,487 discloses the use of gelling compositions in which the odor controlling agents, zeolites and carbon, are incorporated by means of a binder. U.S. Pat. No. 5,211,870 discloses the use of zeolites within a cleansing bar for control of odor. U.S. Pat. No. 4,719,030 discloses a translucent soap bar containing sodium aluminosilicate. All documents cited in this specification are incorporated herein by reference.

SUMMARY OF THE INVENTION

We have found that imides, especially polyimides and more especially polysuccinimides, reduce noxious odors. This reduction by imides is especially effective against amines and ammonia, however, there is also a reduction in odors not known to be odoriferous as a result of amines or ammonia, such as cigarette smoke. Although the mechanism of odor removal, especially in the case of amine or ammonia odors, may be theoretically due to a reaction of the amine or ammonia with the imide, petitioners do not want to be held to this theory of action, as the actual method of odor reduction remains to be firmly established and it is apparent that other molecules may react with the imide and or be absorbed or adsorbed by the imide. Thus, although petitioners believe that the reaction of an amine or ammonia with the imide to be a primary method for the reduction of noxious odors, this reduction may not be limited to those molecules. Reference to the removal of noxious odors by imides may be thought of as scavenging amines or ammonia from the surrounding atmosphere by removal of a quantity of the amine or ammonia by reaction or possibly by absorption or adsorption. Such scavenging might be envisaged as the reaction of an amine from solution or from a gas. Said scavenging might include removal of ammonia or amines that are toxic by such imides after the imide has been immobilized to prevent its release. Such immobilization need not be restricted as to method of immobilization as long as sufficient imide groups remain to react with the desired amine or ammonia for removal from the stream or mixture from which it is to be removed or neutralized. The removal or reduction of the presence of the ammonia or amine by the imide, having reacted to provide a product having no odor, no volatility or low volatility, provides a method for reducing the odor of a solution or gas containing such ammonia or amine. The imide to be used in the present invention should be of sufficient molecular weight or have additional substituents which decrease volatility of the imide, to result in a decrease of the odor of the ammonia or amine upon reaction. The imide may be attached, either mechanically or chemically, to an object of sufficient molecular weight or character to prevent volatilisation of ammonia or the amine to be scavenged. Polyimides of aspartic acid or glutamic acid or mixtures thereof, are especially useful in this respect.

The use of the imides for removal of odor is envisioned to be valuable for incorporation into personal care products such as diapers, both adult and infant, incontinent pads, surgical sponges and dressings, surgical pads, catamenial devices such as sanitary napkins, shields, liners, tampons, meat trays especially for fish, bath mats and the like. Such pads can be composed of polyurethane, cellulose, alginate, gelatin, carrageenan, polystyrene, polyolefin or mixtures thereof and may include additional layers to facilitate use in their respective field The imides can also be incorporated in holding facilities, including foul smelling lagoons, such as those containing animal wastes, or tanks, especially those used for holding human, pig, cattle or other farm wastes, and more especially when the imides are in the form of films or incorporated in films to prevent escape of odors. They can also be used to reduce the odor from sulfite liquor waste ponds or other similar industrial waste treatment facilities. Such reduction can be achieved by mixing the imide with the waste or by depositing the imide on an inert or biodegradable object and mixing the object or allowing the object to come into contact with the waste at the surface, in the body of the waste or on the bottom of the lagoon, holding tank or pond. Thus, the imide can be dispersed on particles, such as clay or other absorbent inorganic or organic materials, for use in controlling odors in animal litter. The imides can be dispersed by spraying or spreading as powders, or held by means of binders. Alternatively, the imide may be retained on a floating object to allow the imide to remain on the surface of a holding facility, such as a pond, lagoon or tank. The floating object may be a film or a particle, especially a biodegradable particle, such as those obtained from corn, rice, wheat, cellulose, soy or rye or fractions thereof or blends thereof, especially when puffed. For sewage in holding facilities, such as portable toilets whether stationary, in planes, trains, boats or mobile homes or the like, floating particles would be advantageous for control of odor as the maximum effect would be available at the liquid-gaseous interface through which the volatiles must pass. Dispersion of the slurries, or solutions or solids on liquid or solid animal wastes including fowl, pig and cattle pens to reduce ammonia and amine levels can prevent harmful effects of the ammonia/amines to the animals as well as reducing the release of objectionable odors to the environment. Solutions or powders may be dispersed on articles or places where animal or human wastes have been deposited, especially urine. Thus, imides can be incorporated into cleaners for rugs or clothing, for solutions for dipping articles, such as clothes, furnishings, shoes, and other items which might easily come into contact with human or animal urine, for removal of odors. Sprays to remove odors from the air can also be prepared. A personal cleansing bar containing an imide provides a method of reducing the odor of materials used in the bars, especially because such bars may be in prolonged contact with air and/or bacteria for long periods of time. Imides are also useful in soap bars and laundry bars. The quantities of imides contained within the bars would be dependent on materials used in the formulation of the bars and detergent formulations. For instance, synthetic cleansing bars contain additional raw materials selected from the group consisting of alkyl sulfate, acyl isethionate, alkyl sarcosinate, alkyl glyceryl ether sulfonate, paraffin wax, sodium acyl sarcosinate, stearic acid, lauric acid, coconut acid, soap, sodium isethionate, sodium chloride, water, cationic polymer and mixtures thereof. The imides are added to the bars at the appropriate point in the manufacture to prevent formation of noxious odors. Such bars might contain 0.01% to 10% imide, depending on the nature of the imide, some of which are useful as surfactants in their hydrolyzed state, and the nature of the odor. Detergents also contain perfumes as masking agents for the odors contained therein. Such odors may be controlled by the addition of the appropriate amount of polysuccinimide, usually 0.01% to 10%, at the appropriate time in the manufacture. Additionally, the imide may be combined with release agents, such as enzymes or hydrolytic bases or acids, to transform the odoriferous chemical to one which will readily deodorize by the addition of an imide. Enzymes such as ureases or other enzymes which produce an amine or ammonia as a byproduct.

The imides formed from aspartic acid and glutamic acid or mixtures thereof or copolymers formed with amines, for instance those obtained in U.S. Pat. Nos. 5,357,004, 5,391,642, 5,408,028, 5,408,029, 5,442,038, 5,466,760, are examples of imides which reduce the odor of amines or ammonia. Imides of high molecular weight, especially those in which the reacted product is insoluble in water due to high molecular weight are especially valuable in the reduction of odor as the materials can be placed behind polymeric barriers or woven or non-woven fabrics through which the amine or ammonia may pass, either in particle form or adsorbed in another material such as cellulose or incorporated in another material such as acrylate polymer, thus preventing the amine or ammonia from coming in contact with the source of the amine or ammonia. An example of this use is in the production of a diaper containing a plastic barrier or woven or non-woven fabrics through which urine and the amines and ammonia responsible for much of the odor can pass to the cellulose floe and optionally the polyacrylate superabsorbent placed there for absorbency, either of which or both may contain the imide or upon which the imide may reside. At high molecular weights and/or with cross-linking, polyimides form a gel upon hydrolysis and are unable to migrate through porous barriers. This in turn not only reduces the odor but also reduces irritation of the skin of the subject wearing the diaper.

Further, such imides would be useful in removing ammonia or amines containing body wastes from the bloodstream, if immobilized or attached to a blood non-reactive material or reacted with a molecule such that the imide-amine reaction product was non-toxic. Such imides might serve as foods, providing a method for removal of nitrogenous wastes that are retained in certain disease states such as those affecting the liver.

Likewise, the imides of the present invention could be incorporated in catamenial devices to reduce the odors thereof Bandages are yet another area where the imides could be used to reduce odor. Pads made of these materials or containing these materials, deposited on the surface or contained within a reservoir, could be used to prevent odor caused by leakage in persons where bladder sphincter control is compromised. Such pads could also be placed in the vents of holding vessels for diapers, sewage or other containers of amines or ammonia to prevent odor escape.

Although it is well known that imides react readily with amines or ammonia, it has not been appreciated that imides could be used to control odor. The reduction of odor wherein the amine or ammonia and the imide are in contact through a solvent in which one or both is soluble is effective. Contact through an aqueous solution or interface is especially effective. Surprisingly, even gaseous amines or ammonia when contacted with solid imide also reduce odors, albeit somewhat more slowly.

The object of this invention is to provide a method for the reduction of odors, especially those due to ammonia or amines. Another object of this invention is to provide a method for the removal of ammonia or amines from aqueous, organic or gaseous streams. Yet another object of this invention is to provide a method of treating animal waste products to reduce or eliminate the ammonia or amine containing components by reaction with a suitable imide. Still another object of this invention is to provide a method of treating personal care products such as diapers, both adult and infant, incontinent pads, surgical sponges and dressings, surgical pads, catamenial devices such as sanitary napkins, shields, liners, tampons, meat trays especially for fish, bath mats and the like, to reduce the odor of the waste products deposited there in normal usage of the product. A further object of this invention is the use of an imide for reduction of odor in animal litter. Yet another object of the invention is the reduction of odor in foul smelling lagoons or holding tanks, such as those containing human or animal wastes, especially those used for holding pig, cattle or other farm wastes, of sulfite liquor waste ponds or other industrial waste treatment facilities where odor control is important. Still another object of the invention is the method of treating the above odors wherein the imides are in the form of films or incorporated in films, gels or solutions to reduce odors. Yet another object of the invention is a method of preventing odors in cleansing bars, soap bars and laundry bars.

DETAILED DESCRIPTION OF THE EMBODIMENTS

EXAMPLE 1

Removal of ammonia fumes in the gaseous state by polysuccinimide

A 5.0 g portion of polysuccinimide powder, approximately 10,000–15,000 molecular weight (m.w.), with 0.05 eq of imide groups, prepared by thermal polymerization of aspartic acid, was dispersed in 2.5 g of cellulose floc obtained from a commercially available disposable baby diaper. The resultant imide/cellulose floc pad was wrapped in a single layer of a cellulose nonwoven membrane to form a circular pad of about 4 inch diameter and ½ inch thickness. A second pad was constructed in the same manner except that the imide was not included.

The pads were placed in separate jars, each containing 0.5 g of 21% $NH_3$ in water solution (0.006 equivalents of $NH_3$) on a filter paper disk of 1.5 inches. The jars were sealed and allowed to stand for 16 hrs at 25° C. Upon opening the jars, a faint odor of $NH_3$ was detected in the jar containing the polysuccinimide while the jar without the succinimide gave off overpowering fumes of ammonia.

The cellulose fibers thus treated can be easily placed in diapers for removal of odor.

EXAMPLE 2

Dispersion of an imide on cellulose fiber

A solution of 2.0 g of polysuccinimide, prepared by thermal polymerization of ammonium maleate according to U.S. Pat. No. 5,288,783, in 10 g of N-methylpyrollidinone was dispersed on 2 g of cellulose fiber obtained from a disposable baby diaper. The resulting slightly damp mass was added to 100 mL of water at 25° C. to give a slurry of fibers containing precipitated polysuccinimide. The solids were collected by filtration and washed with water. The solids were dried for 10 hrs at 65° C. to give 4.5 g of cellulose/polysuccinimide fibers. These fibers were then spread out to form a 4×⅜ inch thick pad held inside a non-woven cellulose membrane pouch (Sample 1). For a control, the experiment was duplicated, but polysuccinimide was not added (Sample 2). The experiment was repeated without drying yielding 15.3 g of damp fibers (Sample 3). The non-dried control was also prepared (Sample 4). The imides were found to be effective in controlling ammonia and amine odors as shown in Example 5.

EXAMPLE 3

Preparation of a polyaspartate gel containing large quantities of polysuccinimide A 2.0 g portion (0.2 equivalents of imide) of a lysine crosslinked polysuccinimide, prepared by the method of U.S. Pat. No. 5,408,029, incorporated herein by reference, was slurried in 30 mL of water containing 0.4 g of NaOH (0.01 equivalents) for 8 hrs at 25° C. to give swollen gel particles having both imide and carboxyl groups. These particles were enclosed in a pouch made from a non-woven cellulose membrane, 4×½ inches (Sample 5). A similar pouch of gel containing completely hydrolyzed lysine crosslinked polyaspartic acid was prepared as a control (Sample 6). The gel containing the imide was found to be effective in controlling ammonia and amine odors as shown in Example 5.

EXAMPLE 4

Mechanical Dispersion of polysuccinimide to cellulose fiber

Finely powdered polysuccinimide, prepared as in Example 2, was dropped onto 2.5 g of cellulose fiber and the whole was enclosed in a membrane pouch of non-woven cellulose (Sample 7). A similar pouch containing no polysuccinimide was prepared as a control (Sample 8). The imide was found to be effective in controlling ammonia and amine odors as shown in Example 5.

EXAMPLE 5

Odor Removal by polysuccinimide

The pouches from Examples 2–4 were placed in separate jars into which 0.25 g of ammonia/amine mixture had been placed on a filter paper disk of 1.5 inches at 10% weight concentrations (1.47 mmoles ammonia, 0.8 mmoles methyl amine, 0.19 mmoles diethyl amine, 0.4 mmoles n-butyl amine). The jars were sealed and allowed to stand for the indicated times at 25° C. Upon opening the jars slightly, the odor was classified as by a 0 to 10 rating in which 10 indicated an overpowering stench and 0 was no odor. At 8, the was rated very strong and at 6 strong while at 4 the odor was moderate and at 2 the odor was slight.

| Time(hrs) | 0 | 0.5 | 1 | 2 | 3 | 4 | 5 | 6 | 12 |
|---|---|---|---|---|---|---|---|---|---|
| Sample 1 | 10 | 9 | 9 | 8 | 7 | 6 | 5 | 4 | 3 |
| Sample 2 | 10 | 10 | 10 | 10 | 10 | 10 | 10 | 10 | 10 |
| Sample 3 | 10 | 8 | 6 | 3 | 3 | 2 | 2 | 2 | 2 |
| Sample 4 | 10 | 9 | 9 | 9 | 9 | 9 | 9 | 9 | 9 |
| Sample 5 | 10 | 8 | 7 | 4 | 3 | 3 | 3 | 2 | 2 |
| Sample 6 | 10 | 9 | 9 | 9 | 9 | 9 | 9 | 9 | 9 |
| Sample 7 | 10 | 9 | 8 | 7 | 6 | 6 | 5 | 4 | 3 |
| Sample 8 | 10 | 10 | 10 | 10 | 10 | 10 | 10 | 10 | 10 |

These results show that the controls, Samples 2, 4, 6, and 10 were ineffective in controlling the odor while the samples containing imides, Samples 1,3,5 and 7 were successful in controlling the noxious amine and ammonia odors.

EXAMPLE 6

Odor Removal by a monomeric imide

A mechanical blend of 5.0 g of phthalimide in 2.5 g of cellulose floc obtained from a disposable diaper was enclosed in a non-woven cellulose membrane pouch, Sample 1a and tested as in Example 5. A control pouch was also prepared containing no imide (Sample 2a) and tested as in Example 5.

| Time(hrs) | 0 | 0.5 | 1 | 2 | 3 | 4 | 5 | 6 | 12 |
|---|---|---|---|---|---|---|---|---|---|
| Sample 1a | 10 | 10 | 9 | 9 | 8 | 7 | 7 | 6 | 6 |
| Sample 2a | 10 | 10 | 10 | 10 | 10 | 10 | 10 | 10 | 10 |

These results show that the control, Sample 2a, was ineffective in controlling the odor while the samples containing the imides, Sample 1a was successful in reducing the noxious amine and ammonia odors.

EXAMPLE 7
Odor Removal by an imide encapsulated in an acrylate hydrogel

A solution of 50 g (0.69 moles) of glacial acrylic acid in 77.5 mL of water was neutralized to a pH of 6.0 with 26 g of NaOH in 48 mL of water. To this solution was added 0.07 g methylene bisacrylamide and 0.04 g ascorbic acid. A 5.0 g portion of this solution was mixed with 4.0 g of an extended chain polysuccinimide/DETA copolymer which contained 2.5% by weight diethylene triamine (DETA). To the resultant mobile slurry was added a solution of 3 mg of ammonium persulfate in 0.5 mL of water. Within minutes, the homogeneous slurry thickened and exothermed to 60° C. After 1 hr at 60° C., a rubber like gel had formed. This gel was cut into 1/16" cubes and dried at 65° C. for 12 hrs to give 6.0 g of red particles. These particles were placed inside a non-woven membrane (Sample 9) and tested as in Example 5. A control without polysuccinimide was also prepared and tested (Sample 10). The performance of each sample in scavenging ammonia and amines was determined.

| Time(hrs) | 0 | 0.5 | 1 | 2 | 3 | 4 | 5 | 6 | 12 |
|---|---|---|---|---|---|---|---|---|---|
| Sample 9 | 10 | 3 | 2 | 2 | 2 | 1 | 1 | 1 | 1 |
| Sample 10 | 10 | 6 | 6 | 5 | 5 | 5 | 5 | 5 | 5 |

The copolymer polysuccinimide encapsulated in an acrylate hydrogel was effective in controlling odors. The acrylate hydrogel was less effective in controlling odor.

EXAMPLE 8
Odor Removal by an imide encapsulated in an acrylate hydrogel

Polysuccinimide powder (4.0 g, prepared by thermal polymerization of L-aspartic acid and phosphoric acid in a mixer) was thoroughly mixed with 1.0 g of dry, crosslinked acrylate gel particles (taken from a disposable baby diaper). This material was placed in a non-woven cellulose membrane pouch and wetted with 10 mL of aqueous 1% NaCl solution to simulate urine (Sample 11). A control material which contained no polysuccinimide was prepared in the same manner (Sample 12). The performance of each sample in scavenging ammonia and amines was determined as in Example 5.

| Time(hrs) | 0 | 0.5 | 1 | 2 | 3 | 4 | 5 | 6 | 12 |
|---|---|---|---|---|---|---|---|---|---|
| Sample 11 | 10 | 4 | 2 | 2 | 2 | 1 | 1 | 1 | 1 |
| Sample 12 | 10 | 8 | 6 | 6 | 5 | 5 | 5 | 5 | 5 |

The polysuccinimide encapsulated in an acrylate hydrogel was effective in controlling odors. The acrylate hydrogel was less effective in controlling odor.

EXAMPLE 9
Odor Removal by an imide incorporated in an acrylate hydrogel

A 25 g portion of an acrylate monomer solution (50 g of glacial acrylic acid, 77.5 mL of water, 26 g of NaOH in 48 mL of water, 0.07 g methylene bisacrylamide and 0.04 g of ascorbic acid) was mixed with polysuccinimide powder (20.0 g, prepared by thermal polymerization of L-aspartic acid and phosphoric acid in a mixer). Ammonium persulfate (15 mg in 0.5 mL of water) was added with good mixing. After 1 hr, in which the temperature had risen to 70° C., a pink rubbery gel formed. After 6 hrs the gel was ground into small pieces and dried for 16 hrs at 65° C., to give 30 g of hard light red particles. A 0.2 g portion of these particles mixing with 20 mL of 1% NaCl in water after which the mix was allowed to stand for 8 hrs at room temperature swelled to 3.0 g or 15 fold The material (Sample 13) and a control material which contained no polysuccinimide prepared in the same manner (Sample 14) were tested as in Example 5, except the amines were replaced with 20 g of urine and 2 g of the Sample were tested.

| Time(hrs) | 6 | 16 |
|---|---|---|
| Sample 13 | 3 | 1 |
| Sample 14 | 8 | 10 |

The imide incorporated in the acrylate hydrogel superabsorbent was effective in reducing odors. The acrylate hydrogel was not effective in controlling odor.

EXAMPLE 10
Cigarette smoke odor removal by an imide incorporated in an acrylate hydrogel A portion of the material prepared in Example 9 containing the polysuccinimide (2.0 g) was placed in a 500 mL jar (Sample 15). A control jar containing the acrylate gel without the polysuccinimide was also prepared (Sample 16). A jar containing no additives was also prepared (Sample 17). An equivalent quantity of cigarette smoke was blown into each jar and the jars were allowed to stand for 8 hours. Upon carefully opening the jars and noting the odor it was found that the stale cigarette odor was considerably reduced in Samples 15 and was not noticeably affected in Samples 16–18. This showed that the imide reduced the odor.

EXAMPLE 11
Enhanced scavenging of amines and ammonia by imides and humectants A slurry of 5.0 g of polysuccinimide prepared from the thermal polymerization of ammonium maleate was mixed with 5.0 g of propylene glycol and mechanically dispersed in 2.5 g of cellulose floc. This material was then placed in a pouch of non-woven cellulose membrane (Sample 18). A similar preparation containing no imide was also prepared (Sample 19). The preparation of a sample in the same manner as for the polysuccinimide was carried out using phthalimide (Sample 20). A similar preparation was also made using no propylene glycol with polysuccinimide as the imide (Sample 21).

| Time(hrs) | 0 | 0.5 | 1 | 2 | 3 | 4 | 5 | 6 | 12 |
|---|---|---|---|---|---|---|---|---|---|
| Sample 18 | 10 | 4 | 3 | 2 | 2 | 2 | 1 | 1 | 1 |
| Sample 19 | 10 | 9 | 7 | 7 | 7 | 7 | 6 | 5 | 4 |

-continued

| Time(hrs)  | 0  | 0.5 | 1 | 2 | 3 | 4 | 5 | 6 | 12 |
|------------|----|-----|---|---|---|---|---|---|----|
| Sample 20  | 10 | 9   | 8 | 6 | 6 | 6 | 6 | 6 | 6  |
| Sample 21  | 10 | 9   | 8 | 7 | 6 | 6 | 5 | 4 | 3  |

These results show that the imides, whether wet or dry were more effective in controlling the odor than the humectant alone, Samples 18, 19 and 21 versus Sample 20.

EXAMPLE 12

Odor control by an imide dispersed on a floating particle

Ten grams of puffed rice (approximately 100 mL) was shaken with 10 g of powdered polysuccinimide prepared by the thermal polymerization of ammonium maleate. As the particles were shaken, 7.0 g of a hot (50°–60° C.) 5% aqueous gelatin solution was sprayed onto the mix, thus retaining the powdered polysuccinimide on the surface of the puffed rice. The product was dried to give 23 g of coated puffed rice. Ten grams of the imide coated particles were placed on the surface of 100 mL of a 50:50 urine:water solution in a 500 mL jar fitted with a screw cap (Sample 22). An appropriate uncoated control was similarly tested (Sample 23). After storage at room temperature for 48 hours the samples were evaluated as in Example 5.

| Time(hrs)  | 0 | 48 |
|------------|---|----|
| Sample 22  | 5 | 3  |
| Sample 23  | 5 | 8  |

The imide coated, floating, puffed rice particles reduced the odor.

It will be apparent to those skilled in the art that the examples and embodiments described herein are by way of illustration and not of limitation, and that other examples may be utilized without departing from the spirit and scope of the present invention, as set forth in the appended claims.

We claim:

1. A method of removing odor comprising contacting said odor with an imide.

2. The method of claim 1 wherein said imide is a polyimide.

3. The method of claim 2 wherein said polyimide is selected from the group of polyimides consisting of polysuccinimide, polyglutarimide, copolymers of polysuccinimide, polyglutarimide, copolymers of polyglutarimide and mixtures thereof.

4. The method of claim 1 comprising contacting said odor with an imide in the presence of a humectant.

5. The method of claim 2 wherein said polyimide is polysuccinimide.

6. A method of removing an ammonia or an amine from a stream comprising contacting said ammonia or amine with an imide.

7. The process of removing undesirable levels of ammonia or an amine from a mammal comprising:

administering to said mammal a sufficient amount of an imide to reduce said level.

8. The method of claim 1 wherein said imide is dispersed over the site of the odor.

9. The method of claim 8 wherein said imide is in solution.

10. The method of claim 8 wherein said site is the air.

11. A method of removing odor comprising contacting said odor with an imide wherein said odor results from ammonia or an amine.

* * * * *